United States Patent [19]

Keefer et al.

[11] Patent Number: 5,366,997
[45] Date of Patent: Nov. 22, 1994

[54] OXYGEN SUBSTITUTED DERIVATIVES OF NUCLEOPHILE-NITRIC OXIDE ADDUCTS AS NITRIC OXIDE DONOR PRODRUGS

[75] Inventors: Larry K. Keefer, Bethesda, Md.; Tambra M. Dunams, Florence, Ala.; Joseph E. Saavedra, Thurmont, Md.

[73] Assignee: The United States of America as represented by the Secretary of the Department of Health and Human Services, Washington, D.C.

[21] Appl. No.: 950,637

[22] Filed: Sep. 23, 1992

Related U.S. Application Data

[63] Continuation-in-part of Ser. No. 764,908, Sep. 24, 1991, abandoned.

[51] Int. Cl.$^5$ .............. A61K 31/13; A61K 31/535; A61K 31/445; C07C 243/04
[52] U.S. Cl. .............. 514/611; 514/238.2; 514/255; 514/315; 514/426; 514/601; 514/929; 544/164; 544/382; 546/244; 548/557; 564/81; 564/113
[58] Field of Search ............ 564/113, 81; 514/611, 514/929, 238.2, 315, 426, 255, 601; 544/164, 382; 546/244; 548/557

[56] References Cited

U.S. PATENT DOCUMENTS

| | | | |
|---|---|---|---|
| 3,153,094 | 10/1964 | Reilly | 260/576 |
| 4,265,714 | 5/1981 | Nolan et al. | 204/11 |
| 4,482,533 | 11/1984 | Keith | 424/28 |
| 4,638,079 | 1/1987 | Inskip et al. | 560/4 |
| 4,708,854 | 11/1987 | Grinstead | 423/235 |
| 4,921,683 | 5/1990 | Bedell | 423/235 |
| 4,952,289 | 8/1990 | Ciccone et al. | 204/129 |
| 4,954,526 | 9/1990 | Keefer | 514/611 |
| 4,985,471 | 1/1991 | Ohta et al. | 522/27 |
| 5,039,705 | 8/1992 | Keefer et al. | 514/611 |
| 5,087,631 | 2/1992 | Shaffer et al. | 514/342 |
| 5,087,671 | 2/1992 | Loeppky et al. | 525/328.2 |
| 5,094,815 | 3/1992 | Conboy et al. | 422/52 |

FOREIGN PATENT DOCUMENTS

| | | |
|---|---|---|
| 0425154A1 | 10/1990 | European Pat. Off. |
| 211789 | 7/1984 | Germany |
| PCT/US89/-02611 | 6/1989 | WIPO |
| WO91/05551 | 5/1991 | WIPO |

OTHER PUBLICATIONS

1991 Article by Maragos, et al., Complexes of NO with Nucleophiles as Agents for the Controlled Biological Release of Nitric Oxide. Vasorelaxant Effects, *J. Med. Chem.*, 34, 3242-3247.
1990 Article by Myers, et al., Vasorelaxant Properties of the Endothelium–Derived Relaxing Factor more closely Resemble S–Nitrosocystein Than Nitric Oxide, *Nature*, vol. 345.
1989 Article by Ignarro, Endothelium–Derived Nitric Oxide: Actions and Properties, *The FASEB Journal*, vol. 3, Jan.
1988 Article by DeFeudis, Endothelium–Dependent Vasorelaxation—A New Basis for Developing Cardiovascular Drugs, *Drugs of Today*, vol. 24, No. 2, pp. 103–115.
1987 Article by Palmer, et al., Nitric Oxide Release Accounts for the Biological Activity of Endothelium–Derived Relaxing Factor, *Nature*, vol. 327 11, Jun.
1987 Article by Kruszyna, et al., Red Blood Cells Generate Nitric Oxide from Directly Acting, Nitrogenous Vasodilators, *Toxicol. Appl. Pharmacol.*, 91, 429–438.
1986 Article by Trissel, Intravenous Infusion Solutions, Handbook on *Injectable Drugs*, Fourth Addition.
1984 Article by Furchgott, The Role of Endothelium in the Responses of Vascular Smooth Muscle to Drugs, *Ann. Rev. Pharmacol, Toxicol*, 24:175–97.
1982 Article by DeLuca, et al., Parenteral Drug-Delivery Systems, *Pharmaceutics and Pharmacy Practice*.
1982 Article by Hansen, et al., N–Nitrosation of Secondary Amines by Nitric Oxide Via the 'Drago Complex', *IARC Sci.*, Publ. No. 41 pp. 21–29.

(List continued on next page.)

*Primary Examiner*—Peter O. O'Sullivan
*Attorney, Agent, or Firm*—Leydig, Voit & Mayer, Ltd.

[57] ABSTRACT

There are disclosed cardiovascularly active compounds possessing antihypertensive properties, and pharmaceutical compositions containing these agents and a method of treating cardiovascular disorders with the compounds. The active components of the pharmaceutical compositions are compounds of formula I

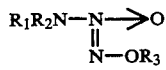

wherein $R_1$ and $R_2$ are independently chosen from straight chain and branched chain alkyl and olefinic groups, which may be unsubstituted or substituted; or $R_1$ and $R_2$ together with the nitrogen atom they are bonded to form a heterocyclic group; and $R_3$ is a pharmaceutically acceptable organic group selected from alkyl and olefinic groups which may be unsubstituted or substituted, acyl, a sulfonyl, sulfinyl, sulfenyl, carbonate, or carbamate derivative; or $R_3$ is a group of the formula—$(CH_2)_n ONN(O)NR_1R_2$, wherein n is 2–8, and $R_1$ and $R_2$ are as described above. Novel compounds are disclosed wherein at least one of $R_1$, $R_2$ and $R_3$ is an olefinic group or heteroatom-substituted straight or branched chain alkyl or olefinic group. Novel methods of synthesizing the compounds are also disclosed.

25 Claims, 1 Drawing Sheet

OTHER PUBLICATIONS

1981 Article by Ignarro, et al., Mechanism of Vascular Smooth Muscle Relaxation by Organic Nitrates, Nitrites, Nitroprusside and Nitric Oxide: Evidence for the Involvement of S-Nitrosothiols as Active Intermediates, *J. Pharmacol. Exp. Ther.*, 218, 739–749.

Article by Lutz, et al., Isolation of Trioxodinitrato (II) Complexes of Some First Row Transition Metal Ions, *J. C. S. Chem. Comm.*

1977 Article by Nakanishi, et al., Participation of Hydrocarbons in the Photodimerization of 3, 4-Dichlorocinnamic Acid, *J. C. S. Chem. Comm.*

1963 Article by Longhi, et al., Metal-Containing Compounds of the Anion $(C_2H_5)_2NN_2O_2-$, *Insrg. Chem.*, vol. 2 Feb.

1962 Article by Drago, Reactions of Nitrogen (II) Oxide, *Advances In Chemistry Series*, No. 36.

1961 Article by Drago, et al., The Reaction of Nitrogen (II) Oxide with Various Primary and Secondary Amines, *Journal of Amer. Chem. Soc.*, vol. 83, Apr. 20.

1990 Article by Garg, et al., Nitric Oxide-Generating Vasodilators Inhibit Mitogenesis and Proliferation of Balb/C3T3 Fibroblasts By A Cyclic GMP-Independent Mechanism, *Biochem. and Biophys. Res. Comm.*, 171, 474–479.

1988 Article by Hibbs, Jr., et al., Nitric Oxide: A Cytotoxic Activated Macrophage Effector Molecule, *Biochem. and Biophys. Res. Comm.*, 157, 87–94.

1981 Article by Holford, et al., Understanding the Dose-Effect Relationship: Clinical Application of Pharmacokinetic-Pharmacodynamic Models, *Clinical Pharmacokinetics*, 6, 429–453.

1990 Article by Ignarro, Nitric Oxide. A Novel Signal Transduction Mechanism for Transcellular Communication, *Hypertension (Dallas)*, 16, 477–483.

1990 Article by Ignarro, Biosynthesis and Metabolism of Endothelium-Derived Nitric Oxide, *Annu. Rev. Pharmacol. Toxicol.*, 30, 535–560.

1985 Article by Ignarro, et al., The Pharmacological and Physiological Role of Cyclic GMP in Vascular Smooth Muscle Relaxation, *Annu. Rev. Pharmacol. Toxicol.*, 25, 171–191.

1989 Article by Kuhn, et al., Endothelium-Dependent Vasodilation in Human Epicardial Coronary Arteries: Effect of Prolonged Exposure to Glycerol Trinitrate or SIN-1, *J. Cardiovasc. Pharmacol.*, 14 (Suppl. 11), S47–S54.

1990 Marletta, et al., Unraveling the Biological Significance of Nitric Oxide, *BioFactors*, 2, 219–225.

1991 Smith, et al., Nitroprusside: A Potpourri of Biologically Reactive Intermediates, *Biological Reactive Intermediates IV. Molecular and Cellular Effects and Thier Impact on Human Health* (Witmer, et al., eds.), Advances in Experimental Medicine and Biology, vol. 283 (Plenum Press, pp. 365–369).

1989 Stuehr, et al., Nitric Oxide: A Macrophage Product Responsible for Cytostasis and Respiratory Inhibition in Tumor Target Cells, *J. Exp. Med.*, 169, 1543–1555.

1977 WHO Task Group on Environmental Health Criteria for Oxides of Nitrogen, *Oxides of Nitrogen*, Environmental Health Criteria 4 (World Health Organization: Geneva).

1990 Article by Wilcox, et al., Effect of Cyanide on the Reaction of Nitroprusside with Hemoglobin: Relevance to Cyanide Interference With the Biological Activity of Nitroprusside, *Chem. Res. Toxicol.*, 3, 71–76.

1992 Article by Stamler, et al., S-Nitrosylation of Proteins With Nitric Oxide: Synthesis and Characterization of Biologically Active Compounds, *Proc. Natl. Acad. Sci., USA*, vol. 89, pp. 444–448, Jan.

1992 Article by Smith, et al., Complex Contractile Patterns in Canine Colon Produced by Spontaneous Release of Nitric Oxide, *Gastroenterology*, vol. 102, No. 4 Part 2, Apr.

1991 Article by Jones, Metastable Polymers of the Nitrogen Oxides. 1. Open Chain Nitric Oxide Analogues of Polythlazyl: A MNDO/AM1 Study, *J. Phys. Chem.*, 95, 2588–2595.

1981 Article by Middleton, et al., Further Studies on the Interaction of Nitric Oxide With Transition-Metal Alkyls, *J. C. S. Dalton*, pp. 1898–1905, Feb. 6.

1989 Article by Bonakdar, et al., Continuous-Flow Performance of Carbon Electrodes Modified With Immobilized Fe(II)/Fe(III) Centers, *Calanta*, vol., 36, No. 1/2, pp. 219–225.

1992 Article by Park, et al., Controlled Protein Release from Polyethyleneimine-Coated Poly (L-lactic Acid)/-Pluronic Blend Matrices, *Pharmaceutical Research*, vol. 9, No. 1.

1932 Uber Reaktionen und Eigenschaften des Stickoxyds und seiner Verbindungen, II. Mitteil: Zur Kenntnis der Salze Der stickoxyd-schwefligen Saure, Heinz Gehlen, *Aus D. Chem. Institut D. Universitat Konigsberg* I. PR., Eingegaugen am 1. Juni.

1932 Der Raman-Effekt als Grundlage einer organischen Spektralanalyse (I. Mitteil.), Birchkenbach, et al., *Aus D. Chem. Institut D. Betgakademie Clausthal*, Eingegaugen am 9, Juni.

1987 Synthesis of 1-Alkoxy-3,3-Dialkyltriazene 2-Oxides from Alkoxyamines and Nitrosoamines, Artsybasheva, et al., A. A. Zhdanov Leningrad State University, Translated from Zhurnal Organicheskoi Khimii, vol. 28, No. 6, pp. 1168–1173, Jun., Original article submitted May 28, 1986.

Kuznetsov et al., "Photoelectron spectra and electronic structures of 2-alkoxy-1-*tert*-alkydiazen-1-oxides and 1-alkoxy-3,3-dialkyltriazen-2-oxides," *J. Molecular Structure*, 263, 329–341.

Saavedra et al., "Secondary Amine/Nitric Oxide Complex Ions, $R_2N[N(O)NO]$-O-Functionalized Chemistry," *J. Org. Chem.*, 57, 6134–6138 (1992).

OXYGEN SUBSTITUTED DERIVATIVES OF NUCLEOPHILE-NITRIC OXIDE ADDUCTS AS NITRIC OXIDE DONOR PRODRUGS

This application is a continuation-in-part of copending patent application Ser. No. 07/764,908 filed Sep. 24, 1991 now abandoned.

FIELD OF THE INVENTION

The present invention generally relates to the treatment of patients suffering from cardiovascular disorders requiring a lowering of the blood pressure. Certain novel compounds and pharmaceutical compositions which release nitric oxide on in vivo activation are utilized in the method.

BACKGROUND OF THE INVENTION

Endothelium-derived relaxing factor (EDRF) is a labile humoral agent which is part of a cascade of interacting agents involved in the relaxation of vascular smooth muscle. EDRF is thus important in the control of vascular resistance to blood flow and in the control of blood pressure. Some vasodilators act by causing EDRF to be released from endothelial cells. (See Furchgott, Ann. Rev. Pharmacol. Toxicol. 24, 175–197, 1984.) Recently, Palmer et al. have presented evidence suggesting that EDRF is identical to the simple molecule, nitric oxide, NO (Nature 317, 524–526, 1987), though there remains controversy on this point. It has been hypothesized for years that many nitrovasodilators that mimic the effect of EDRF, like glyceryl trinitrate, amyl nitrite, $NaNO_2$, and sodium nitroprusside (SNP), do so by virtue of their conversion to a common moiety, namely NO, which is also a vasodilator. (See Kruszyna et al., Tox. & Appl. Pharmacol. 91, 429–438, 1987; Ignarro, FASEB J. 3, 31–36, 1989; Ignarro et al., J. Pharmacol. Exper. Therapeutics 218 (3), 739–749, 1981.)

Some of the compounds suitable for use in the method of the present invention are previously described in scientific literature. However, there is no suggestion in the prior art that any of the disclosed compounds are antihypertensive; indeed there is no suggestion in the prior art that they have any pharmaceutical use. Four compounds are described in Reilly, U.S. Pat. No. 3,153,094, and in Longhi and Drago, Inorg. Chem. 2, 85–88, 1963, and four compounds are disclosed in Artsybasheva and Ioffe, J. Org. Chem. U.S.S.R. (Engl. transl., 23, 1056–1060, 1987). Each of these references is incorporated by reference herein in its entirety. The references teach no biological activity for the compounds disclosed.

Related inventions (to the present invention) are described in U.S. patent application Ser. Nos. 07/316,958, filed Feb. 28, 1989 (now U.S. Pat. No. 4,954,526), 07/409,552, filed Sep. 15, 1989 (now U.S. Pat. No. 5,039,705), 07/423,279, filed Oct. 18, 1989, 07/585,793, filed Sep. 20, 1990, 07/743,892, filed Aug. 12, 1991, 07/764,906, filed Sep. 24, 1991, 07/764,908, filed Sep. 24, 1992, 07/858,885, filed Mar. 27, 1992, 07/867,759, filed Apr. 18, 1992, and 07/935,565, filed Aug. 24, 1992, each of which is incorporated herein by reference.

SUMMARY OF THE INVENTION

It has now been discovered that a class of compounds of the structure:

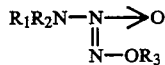

wherein $R_1$–$R_3$ are organic moieties defined below, are long-acting cardiovascular agents and thus are useful for treating cardiovascular disorders in which lowering the blood pressure has a beneficial result. It is believed that these compounds function by metabolic cleavage of the $R_3$ group to produce an anion that releases NO in the blood after administration to a mammal; however, the invention should not be limited by this hypothesis.

The present invention will become more fully understood from the detailed description given here and below and the accompanying drawing which is given by way of illustration only, and thus is not limitative of the present invention.

DETAILED DESCRIPTION OF THE INVENTION

Figure 1:
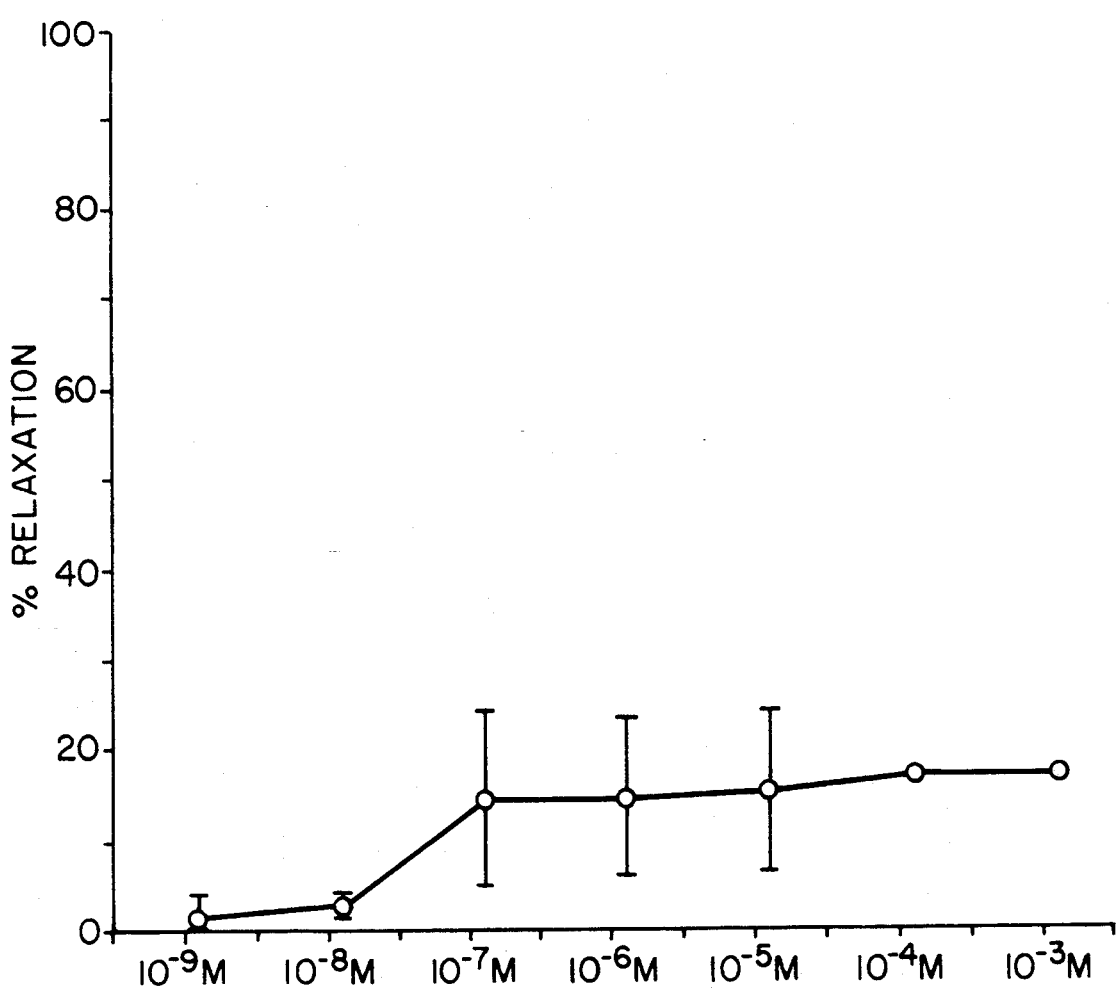
FIG. 1—shows the dose response curve for $Et_2$-N—N(O)NOEt, which was obtained by testing the compound via a standard isolated vascular ring preparation.

The present invention provides for pharmaceutical compositions comprising a compound of formula I,

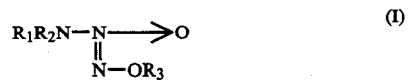

(I)

wherein $R_1$ and $R_2$ are independently chosen from $C_{1-12}$ straight chain alkyl, $C_{1-12}$ alkoxy or acyloxy substituted straight chain alkyl, $C_{2-12}$ hydroxy or halo substituted straight chain alkyl, $C_{3-12}$ branched chain alkyl, $C_{3-12}$ hydroxy, halo, alkoxy, or acyloxy substituted branched chain alkyl, $C_{3-12}$ straight chain olefinic and $C_{3-12}$ branched chain olefinic which are unsubstituted or substituted with hydroxy, alkoxy, acyloxy, halo or benzyl, or $R_1$ and $R_2$ together with the nitrogen atom to which they are bonded form a heterocyclic ring selected from the group consisting of:

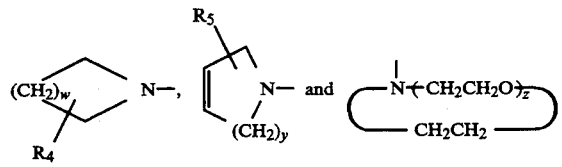

wherein w is 1 to 12, y is 1 or 2, z is 1 to 5, $R_4$ is hydrogen, $C_{1-8}$ straight chain alkyl, $C_{3-8}$ branched chain alkyl, $C_{3-8}$ cycloalkyl, unsubstituted or substituted aryl, such as phenyl, tolyl or the like, and $R_5$ is hydrogen, $C_{1-6}$ straight chain alkyl or $C_{3-6}$ branched chain alkyl; and $R_3$ is a group selected from $C_{1-12}$ straight chain and $C_{3-12}$ branched chain alkyls which are unsubstituted or substituted by hydroxy, halo, acyloxy or alkoxy, $C_{2-12}$ straight chain or $C_{3-12}$ branched chain olefinic which are unsubstituted or substituted by halo, alkoxy, acyloxy or hydroxy, $C_{1-12}$ unsubstituted or substituted acyl, a sulfonyl, sulfinyl, sulfenyl, or carbonate derivative, and a carbamate derivative, as for example, carboxamido; or $R_3$ is a group of the formula $-(CH_2)_n-ON=N(O)NR_1R_2$, wherein n is an integer of 2-8, and $R_1$ and $R_2$ are as defined above; with the proviso that $R_1$, $R_2$ and $R_3$ do not contain a halo or a hydroxy substituent $\alpha$ to a nitrogen or an oxygen atom; and a pharmaceutically acceptable carrier. By straight chain alkyl is meant the non-branched methyl, ethyl, n-propyl, n-butyl, n-decyl, and similar groups. By branched chain alkyl is meant groups like 3-methylpentyl, 2-ethylbutyl, etc.

The compounds of Formula I are long-acting cardiovascular antihypertensives. They are useful for lowering the blood pressure and treating any cardiovascular disorder in which a lowering of the blood pressure has a beneficial effect. As such, the invention also provides an effective method of lowering the blood pressure in a patient in need thereof by administering a pharmaceutical composition containing an effective amount of a compound of Formula I to the patient in need thereof.

Many of the compounds of Formula I, including, for example, wherein $R_1$, $R_2$ or $R_3$ are a heteroatom-substituted (e.g., hydroxy, halo, alkoxy, or acyloxy substituted) straight or branched chain alkyl, or an olefinic group, are novel.

The methods of synthesis of the Formula I compounds are in many cases similar to those disclosed by Reilly, U.S. Pat. No. 3,153,094. Other examples are best obtained by N-derivatization of the 0-alkylated primary amine complexes (Formula I, $R_1 = H \neq R_2$) disclosed in U.S. Pat. No. 4,954,526. In addition, novel synthesis methods are provided herein. The following Experimental Section and the Examples therein illustrate some of the procedures which may be utilized to prepare compounds encompassed hereby. The following Examples, however, are not limiting to the present invention.

EXPERIMENTAL

Proton NMR spectra were recorded using a Varian XL-200 Spectrometer. Spectra were obtained in deutero-chloroform. Chemical shifts ($\delta$) are reported in parts per million (ppm) downfield from tetramethylsilane. Low and high resolution mass spectral (MS) measurements were carried out on a VG-Micromass Model 7070 Mass Spectrometer. The IR spectra were obtained on a Perkin-Elmer 467 spectrophotometer. Gas chromatographic analyses were carried out on a Shimadzu Model 4BM gas chromatograph equipped with a Hewlett-Packard 18652A A/D converter coupled to the recorder of a flame ionization detector. A 10% Carbowax 20M (+2% KOH) on 80/100 Gaschrom Q glass column was used unless otherwise specified. Ultraviolet (uv) spectra were run as ethanolic or aqueous solutions on a Beckman MV1 spectrophotometer unless specified otherwise. Elemental analyses were done at Galbraith Laboratories Inc. (Knoxville, Tenn.), and at Atlantic Microbe (Norcross, Ga.).

EXAMPLE 1

1-n-PROPOXY-2-OXO-3,3-DIETHYL-1-TRIAZENE [$(C_2H_5)_2NN_2O_2(C_3H_7)$]

A partial solution of 1.55 g (0.01 mol) of 2,2-diethyl-1-nitroso-1-oxyhydrazine sodium salt (i.e., 3,3-diethyl-1,2-dioxotriazene, monosodium salt) in 10 ml of anhydrous N,N-dimethylformamide (DMF) was treated with 1.46 ml (0.015 mol) of n-propyl iodide at 25° C. Within 5 minutes of stirring a homogeneous solution resulted, which gradually formed a precipitate (NaI) upon further reaction. The reaction mixture was stirred at room temperature overnight. To this was added 20 ml of distilled water, and the product was extracted into ether and dried over sodium sulfate. Gas liquid chromatographic (GLC) analysis of the solution gave the following relative composition: 43% DMF, 1% nitrosodiethylamine, and 56% 1-n-propoxy-2-oxo-3,3-diethyl-1-triazene. The solution was filtered through a pad of magnesium sulfate, and the solvent was removed on a rotary evaporator. The residual oil was fractionally distilled under vacuum to give 601 mg (33%) of pure product: bp 70°-72° C. at 0.5 mmHg; NMR, $\delta 0.972$ (t,3H), 1.093 (t,6H),1.7945 (m,2H), 3.079 (q,4H), 4.235 (t,2H); IR(film) 2980, 2945, 2885, 1505, 1384, 1230, 1143, 1066, 1005, 841 cm$^{-1}$; uv, $\lambda_{max}(\epsilon)$, 237 (8.049); MS, m/z (%), 176 (M+H, 1), 145 (1), 132 (1), 103 (100), 102 (16), 87 (4), 75 (38), 58 (3), 57 (6), 56 (13), 47 (12), 44 (32), 43 (62), 42 (22), 41 (27). Exact mass: calculated for $C_7H_{18}N_3O_2$, 176.1499; found for MH$^+$, 176.1410. Analysis: C, H, N. Calculated for $C_7H_{17}N_3O_2$: C, 48.00; H,9.71; N,24.00. Found: C,47.80; H,9.39; N,23.54.

EXAMPLE 2

1-METHOXY-2-OXO-3,3-DIETHYL-1-TRIAZENE [$(C_2H_5)_2NN_2O_2CH_3$]

To a solution of 2.24 g (0.014 mol) of 2,2-diethyl-1-nitroso-1-oxyhydrazine sodium salt in 14 ml of absolute methanol was slowly added 1.99 ml (0.021 mol) of dimethyl sulfate. The reaction was distinctly exothermic, and the resulting solution was stirred at 25° C. for 72 hours. The methanol was evaporated in vacuo; the residue was taken up in 20 ml of distilled water and extracted with dichloromethane. The organic layer was separated, dried over sodium sulfate and filtered through a layer of magnesium sulfate. The solvent was removed on a rotary evaporator and the residual oil was vacuum distilled to give 469 mg (23%) of 1-methoxy-2-oxo-3,3-diethyl-1triazene: bp 44° C. at 0.7 mmHg; NMR, $\delta 1.101$ (t, 6H), 3.102 (q,4H), 4.058 (s,3H); IR (film) 2989, 2945, 2875, 1500, 1450, 1383, 1230, 1143, 1058, 1000, 935, 840 cm$^{-1}$; uv, $\lambda_{max}(\epsilon)$, 234 nm (7.945); MS, m/z (%), 147 (M+3), 103(6), 102(100), 87(27), 86(2), 85(5), 84(4), 74(3), 71(3), 58(4), 57(32), 56(33), 54 (92), 42(44), 41(8). Exact mass: calculated for $C_5H_{14}N_3O_2$, 148.1086; found for MH$^+$, 148.1109. Analysis: C, H, N. Calculated for $C_5H_{13}N_3O_2$: C, 40.82; H, 8.84; N, 28.57. Found: C, 40.81; H, 8.86; N, 28.62.

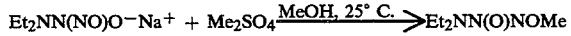

EXAMPLE 3

1-(2-HYDROXYPROPOXY)-2-OXO-3,3-DIETHYL-1-TRIAZENE [$(C_2H_5)_2NN_2O_2CH_2CH(OH)CH_3$]

To a slurry of 4.2 g (0.027 mol) of 2,2-diethyl-1-nitroso1-oxyhydrazine sodium salt in anhydrous tetrahydrofuran was added 2.1 ml (0.03 mol) of propylene oxide. The slurry was stirred at reflux for 20 hours. The reaction was treated with 20 ml of distilled water and the tetrahydrofuran was removed on a rotary evaporator. The aqueous layer was extracted with dichloromethane, dried over sodium sulfate, filtered through a pad of magnesium sulfate and evaporated in vacuo. The residual oil was vacuum distilled to give 298 mg (6%) of product: bp 140° C. at 0.7 mmHg. As an alternative, a more efficient purification procedure than vacuum distillation was developed. The product was chromatographed on dry packed Activity III silica gel, eluted with 2:1 dichloromethane:ethyl acetate, and recovered from the eluate by evaporating the solvent: NMR, δ1.100 (t,6H), 1.2205 (d,3H), 3.122 (q,4H), 4.103–4.264 (3H,m); IR (film), 3430, 2990, 2960, 2880, 1500, 1454, 1370, 1230, 1058, 1010, 952, 845 cm$^{-1}$; uv, $\lambda_{max}$ (ε), 236 (7,204); MS, m/z (%), 192 (MH+,7), 132 (8), 164 (14), 103 (100), 102 (66), 86 (22), 84 (34), 75 (53), 59 (53), 58 (11), 57 (16), 56 (26), 49 (52), 47 (15), 45 (69), 44 (75), 43 (23), 42 (44), 41 (39). Exact mass: calculated for $C_7H_{18}N_3O_3$, 192.1348; found for MH+, 192.1417.

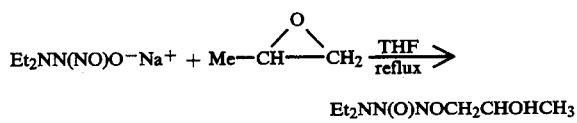

Et$_2$NN(O)NOCH$_2$CHOHCH$_3$

EXAMPLE 4

1-ETHOXY-2-OXO-3,3-DIETHYL-1-TRIAZENE [(CH$_2$H$_5$)$_2$NN$_2$O$_2$C$_2$H$_5$]

To a solution of 19.26 g (0.124 mol) 2,2-diethyl-1-nitroso-1-oxyhydrazine sodium salt in 100 ml of freshly distilled (from Mg) methanol was added 31 g (0.2 mol) of diethyl sulfate dropwise, with stirring. The resulting heterogeneous mixture was stirred for 18 hours at 25° C. The reaction mixture was evaporated in vacuo and the residual blend was extracted with dichloromethane. The organic layer was washed with aqueous sodium hydroxide solution, dried over sodium sulfate and filtered through a layer of magnesium sulfate. The solvent was removed on a rotary evaporator and the residue was vacuum distilled to give 8.9 g (45%) of a pale yellow product: bp 52° C. at 0.7 mmHg; NMR, δ1.097 (t,6H), 1.39 (t,3H), 3.086 (q,4H), 4.34 (q,2H); IR (film) 2985, 2940, 2905, 1510, 1450, 1390, 1230, 1200, 1060, 1010, 925, 830 cm$^{-1}$; uv, $\lambda_{max}$ (ε), 235 nm (6717); MS, m/z (%), 162 (MH+, 100), 161 (M+, 7), 145 (30), 131 (16), 127 (12), 103 (34), 99 (3), 73 (21), 72 (96), 44 (44).

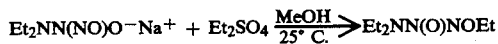

EXAMPLE 5

1-ALLYLOXY-2-OXO-3,3-DIETHYL-1-TRIAZENE [(C$_2$H$_5$)$_2$NN$_2$O$_2$CH$_2$CH=CH$_2$]

A solution of 2.48 g (0.016 mol) of 2,2-diethyl-1-nitroso-1-oxyhydrazine sodium salt in anhydrous N,N-di-methylformamide (DMF) was cooled to 0° C. To the solution was added 1.73 ml (0.02 mol) of allyl bromide dropwise; the solution was allowed to warm up gradually to room temperature and stirred overnight under nitrogen. The reaction mixture was dissolved in 75 ml of water and extracted with ether. The organic layer was dried over sodium sulfate and filtered through a layer of magnesium sulfate; the solvent was removed on a rotary evaporator. The residual oil was vacuum distilled to give 1.01 g (36%) of product: bp 76°-7° C. at 0.6 mmHg; IR(film) 3090, 2985, 2910, 2880, 1510, 1450, 1385, 1235, 1060, 1020, 1000, 940, 845 cm$^{-1}$; uv, $\lambda_{max}$ (ε), 243 (8.868); NMR, δ1. 091 (t,6H), 3. 094 (q,4H), 4.734 (t,1H), 4. 764 (t,1H), 5.333 (m,2H), 6.024 (m,1H); MS, m/z(%), 174 (MH+, 3), 157(2), 143(40), 132(26), 103(25), 102(100), 99(2), 98(30), 87(16), 85(9), 75(5), 57(20), 56(36), 44 (82) 42(83). Exact mass: calculated for C$_7$H$_{15}$N$_3$O$_2$, 173.1164; found for M+, 173.1135.

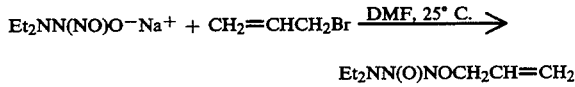

EXAMPLE 6

1-(METHOXYMETHYLENEOXY)-2-OXO-3,3-DIETHYL-1-TRIAZENE [(C$_2$H$_5$)$_2$NN$_2$O$_2$CH$_2$OCH$_3$]

To a slurry of 3.5 g (0.023 mol) of 2,2-diethyl-1-nitroso-1-oxyhydrazine sodium salt in 40 ml of anhydro THF was added 3 g of anhydrous sodium carbonate. The well-stirred mixture was cooled to 0° C. followed by the dropwise addition of chloromethylmethylether. The ice-bath was removed and the reaction mixture was stirred at room temperature under argon for 72 h. The solvent was removed on a rotary evaporator to give 1.89 g of an amber liquid. The crude product was vacuum distilled to give 1.68 g (41% ) of 1- (methoxymethyleneoxy)-2-oxo-3,3-diethyl-1-triazene: bp 67°–68° C. at 1.2 mmHg; NMR, δ1.113 (t,6H), 3.1645 (q,4H), 3.498 (s,3H), 5.262 (s,2H); IR(film) 2985, 2940, 1515, 1440, 1380, 1235, 1165, 970 cm$^{-1}$, uv (MeOH), $\lambda_{max}$(ε), 227 (6,511); MS, m/z (%), 147 (M+-30, 5), 117 (M+-60, 100), 102 (48), 97 (10), 89 (7), 87 (15), 86 (42), 73 (14), 72 (21), 71 (20), 70 (13), 61 (13), 58 (63), 57 (72), 56 (99). Analysis: C, H, N. Calculated for C$_6$H$_{15}$N$_3$O$_3$: C, 40.68; H, 8.47; N, 23.73. Found: C, 40.69; H, 8.65; N, 23.90.

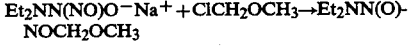

EXAMPLE 7

1-(2-HYDROXYETHOXY)-2-OXO-3,3-DIETHYL-1-TRIAZENE (C$_2$H$_5$)$_2$NN$_2$O$_2$CH$_2$CH$_2$OH

To a slurry of 1.51 g (0.0097 mol) of 2,2-diethyl-1-nitroso-1-oxyhydrazine sodium salt in 20 ml of anhydrous THF was added 1.42 ml (0.02 mol) of freshly distilled 2-bromoethanol. The reaction mixture was heated at reflux, under nitrogen overnight. The mixture was allowed to cool to room temperature and the solvent was removed on a rotary evaporator. The residue was chromatographed on silica gel and eluted with 1:1 dichloromethane:ethyl acetate. The fractions were analyzed by GLC using 3% OV-17 as the stationary phase. The solutions containing the product were combined and evaporated in vacuo to give 160 mg of product: IR (film) 3445, 2990, 2950, 2880, 1505, 1455, 1285, 1065, 1015, 890 cm$^{-1}$; NMR (CDCl$_3$), δ1.105 (t,6H), 3.127 (q,4H), 3.920 (m,2H), 4.391 (m,2H); MS, m/z (%), 178 (MH+, 3), 147 (1), 132 (9), 118 (2), 104 (5), 103 (100), 102 (56), 87 (10), 75 (6), 76 (3), 75 (29), 73 (3), 73 (6), 71 (14), 57 (14), 56 (20), 55 (5). Exact mass: calculated for C$_6$H$_{16}$N$_3$O$_3$, 178.1191; found for MH+, 178.1188.

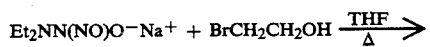

-continued

Et$_2$NN(O)NOCH$_2$CH$_2$OH

EXAMPLE 8

1-(2-BROMOETHOXY)-2-OXO-3,3-DIETHYL-1-TRIAZENE (C$_2$H$_5$)$_2$NN$_2$O$_2$CH$_2$CH$_2$Br

A partial solution of 2.7 g (17.4 mmol) of 2,2-diethyl-1-nitroso-1-oxyhydrazine sodium salt in 17 ml of DMF was cooled to 0° C. under a stream of nitrogen. A solution of 1.4 ml of 1,2-dibromoethane in anhydrous THF was added dropwise. Once addition was complete the ice bath was removed, and the resulting mixture was stirred at 25° C. overnight. To the reaction mixture was added 200 ml of water and the product was extracted with ether. The organic layer was separated and washed with water. The solution was dried over sodium sulfate and filtered through a layer of magnesium sulfate. Evaporation of the solvent gave 2.1 g of crude product. The product was chromatographed through silica gel and eluted with dichloromethane to give 706 mg of pure 1-(2-bromoethoxy)-2-oxo-3,3-diethyl-1-triazene: IR (film) 2980, 2965, 2880, 1510, 1500, 1450, 1383, 1241, 1235, 1070, 1005 cm$^{-1}$; NMR, δ1.104 (t,6H), 3.124 (q,4H), 3.582 (t,2H), 4.522 (m,2H); uv, $\lambda_{max}(\epsilon)$, 233 (8,977); MS, m/z (%), 242 (MH$^+$, $^{81}$Br, 8), 240 (MH$^+$, $^{79}$Br, 9), 224 (4), 223 (4), 211 (37), 209 (36), 132 (41), 109 (56), 107 (56), 101 (64), 102 (100), 84 (32), 72 (32), 56 (36). Exact mass: calculated for C$_6$H$_{14}$$^{81}$BrN$_3$O$_2$, 242.0327, and for C$_6$H$^{79}$BrN$_3$O$_2$, 240.0347; found for MH$^+$, 242.0356 and 240.0417.

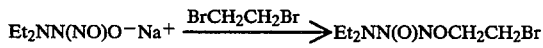

EXAMPLE 9

SYNTHESIS OF FORMULA I COMPOUNDS BY N-SUBSTITUTION OF 1-ALKOXY-2-OXO-3-ALKYL-1-TRIAZENES

Synthesis of starting material, 1-methoxy-2-oxo-3-isopropyl-1-triazene [(CH$_3$)$_2$CHNHN$_2$O$_2$CH$_3$].

A solution of 9.2 g (0.065 mol) of 2-isopropyl-1-nitroso-1-oxyhydrazine sodium salt in 65 ml of anhydrous methanol was cooled to 0° C. To the cold solution was added 5 ml (0.07 mol) of freshly distilled dimethyl sulfate, and the mixture was stirred in the cold for 1 hour. The ice bath was removed and the resulting solution was stirred at 25° C. overnight. The solvent was removed on a rotary evaporator; the residue was taken up in dichloromethane and washed with 5% aqueous sodium hydroxide solution. The organic layer was dried over sodium sulfate and filtered through a pad of magnesium sulfate; the solvent was removed in vacuo. The residual oil crystallized on standing at 0° C. and was recrystallized from ether to give 3.64 g (42%) of 1-methoxy-2-oxo-3-isopropyl-1-triazene: mp 29°–30° C.; IR (film), 3245, 2982, 2950, 1570, 1468, 1390, 1275, 1205, 1605, 1012, 830 cm$^{-1}$; uv (H$_2$O), $\lambda_{max}(\epsilon)$, 242 nm (6,495); NMR, δ1.184 (d,6H), 3.93 (m,1H), 3.977 (s,3H), 5.90 (b,1H); MS, m/z(%), 133 (M$^+$, 6), 132 (11), 118 (32), 102 (18), 88 (42), 87 (7), 86 (10), 85 (8), 73 (6), 61 (9), 60 (5), 57 (12), 56 (17), 49 (21), 47 (20), 45 (32), 44 (7), 43 (100). Exact mass: calculated for C$_4$H$_{11}$N$_3$O$_2$, 133.0851; found for M$^+$, 133.0859.

i-PrNHN(NO)O$^-$Na$^+$ + Me$_2$SO$_4$ $\xrightarrow[\text{0° to 25° C.}]{\text{MeOH}}$ i-PrNHN(O)NOMe

EXAMPLE 9A

1-METHOXY-2-OXO-3-ISOPROPYL-3-METHYL-1-TRIAZENE (CH$_3$)$_2$CHN(CH$_3$)N$_2$O$_2$CH$_3$

To a solution of 200 mg (1.5 mmol) of the 1-methoxy-2-oxo-3-isopropyl-1-triazene prepared above in 1.5 ml of anhydrous THF and 0.5 ml of N,N-dimethylformamide (DMF) was added 200 mg of finely powdered sodium hydroxide. The resulting mixture was stirred at room temperature for 15 minutes, then treated with 0.187 ml (3 mmol) of methyl iodide and stirred for 12 hours at 25° C. under nitrogen. To the reaction mixture was added 10 ml of water and the product was extracted with ether. The solution was dried over sodium sulfate, filtered, and concentrated under vacuum. The crude product was purified on silica gel using 5:1 dichloromethane:ethyl acetate as the eluant. Fractions were monitored by gas chromatographic analysis on a 3% OV-210 packed glass column. The fractions containing the product were combined and concentrated. The residual oil was vacuum distilled to give a 60% yield of 1-methoxy-2-oxo-3-isopropyl-3-methyl-1-triazene: bp 52° C. at 1 mmHg; IR (film), 2980, 2940, 2880, 1500, 1450, 1370, 1250, 1060, 1001, 940, 738 cm$^{-1}$; uv (H$_2$O), $\lambda_{max}(\epsilon)$, 236 (6,391); NMR, δ1.126 (d,6H), 2.840 (s,3H), 3.861 (m,1H), 4.028 (s,3H); MS, m/z (%), 147 (M$^+$, 3), 132 (32), 102 (47), 97 (11), 95 (8), 91 (7), 88 (3), 87 (14), 85 (24), 71 (70), 70 (9), 69 (19), 68 (4), 67 (8), 60 (12), 57 (51), 56 (36), 55 (32), 49 (13), 45 (27), 43 (100), 42 (34). Exact mass: calculated for C$_5$H$_{13}$N$_3$O$_2$, 147.1007; found for M$^+$, 147.0982.

i-PrNHN(O)NOMe $\xrightarrow[\text{THF—DMF}]{\text{NaOH, MeI}}$ i-PrN(Me)N(O)NOMe

EXAMPLE 9B

1-METHOXY-2-OXO-3-ISOPROPYL-3-ALLYL-1-TRIAZENE (CH$_3$)$_2$CHN(CH$_2$—CH=CH$_2$)N$_2$O$_2$CH$_3$

To a solution of 399 mg (3 mmol) of 1-methoxy-2-oxo-3-isopropyl-1-triazene in 20 ml of anhydrous THF was added 1 g of powdered sodium hydroxide. To the stirred mixture was added 433 μl (5 mmol) of allyl bromide; the mixture was heated at reflux under nitrogen for 2 hours. The mixture was evaporated to dryness, and the residue was extracted with dichloromethane. The extract was washed with aqueous sodium bisulfite, dried over sodium sulfate, and filtered through a layer of magnesium sulfate. Evaporation of the solvent gave 454 mg of a brown oil. The oil was chromatographed through silica gel and eluted with 5:1 dichloromethane:ethyl acetate to give 345 mg of an orange oil. This oil was further purified by fractional vacuum distillation to give 180 mg of pure 1-methoxy-2-oxo-3-isopropyl-3-allyl-1-triazene as a pale yellow oil: bp 74° C. at 1.9 mmHg; IR (film) 3085, 2982, 2942, 1502, 1460, 1445, 1390, 1238, 1065, 1006, 942 cm$^{-1}$; NMR, δ6 1.162 (d,6H), 3.474 (septet, 1H), 3.646 (d,2H), 4.027 (s,3H), 5.204 (m,2H), 5.832 (m,1H).

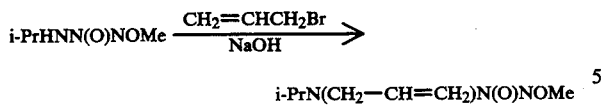

i-PrN(CH₂—CH=CH₂)N(O)NOMe

EXAMPLE 10

1-METHOXY-2-OXO-3-METHYL-3-(2-HYDROXY-PROPYL)-1-TRIAZENE
CH₃CHOHCH₂N(CH₃)N₂O₂CH₃

A solution of 10 g (0.112 mol) of N-methyl-N-(2-hydroxypropyl)amine in 10 ml of triethylamine and 20 ml of petroleum ether was placed in a Parr bottle. The solution was cooled to −80° C. and evacuated, then charged with 60 psi of nitric oxide. After 72 hours the pressure was released and the reaction mixture was flushed with nitrogen. To the mixture was added 20 ml of 25% sodium methoxide in methanol. The mixture was stirred for 10 minutes and the petroleum ether was removed on a rotary evaporator. The residue was taken up in 75 ml of methanol and cooled at 0° C., followed by the dropwise addition of 10 ml of dimethyl sulfate. The mixture was concentrated on a rotary evaporator, and the residue was treated with 50 ml of 10% NaOH. The solution was extracted with dichloromethane, dried over sodium sulfate, and filtered through a layer of magnesium sulfate. Evaporation of the solvent gave 1.47 g of crude product. The crude material was chromatographed on silica gel and eluted with 2:1 dichloromethane:ethyl acetate to give 1.2 g of product: NMR, δ1.199 (d,3H), 1.922 (m, 1H), 3.015 (s,3H), 3.303 (m,2H), 3.969 (m, 1H), 4.033 (s,3H); IR (film), 3450, 2980, 2945, 1595, 1450, 1340, 1230, 1060, 978, 860, 770 cm⁻¹; uv (H₂O), λ_max(ε), 237 nm (5,759).

MeCHOHCH₂N(Me)N(O)NOMe

EXAMPLE 11

Utilizing the procedure set forth in Example 1, and substituting one of the following compounds for 2,2-diethyl-1-nitroso-1-oxyhydrazine sodium salt:

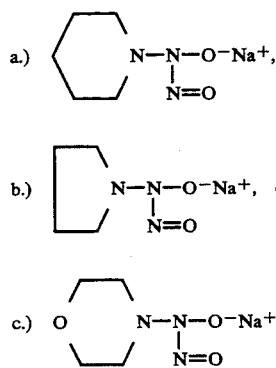

there are obtained, respectively:

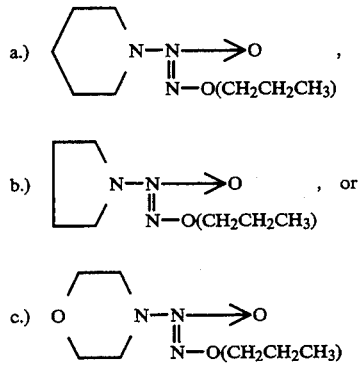

EXAMPLE 12

Utilizing the procedures set forth in Example 1, and substituting the following compound for 2,2-diethyl-1-nitroso-1-oxyhydrazine sodium salt:

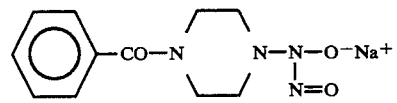

there is obtained the corresponding n-propyl ether compound, which is thereafter subjected to a base hydrolysis reaction, whereby there is obtained the following compound of Formula I.

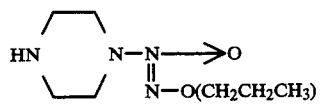

EXAMPLE 13

1,3-BIS(3,3-DIETHYL-2-OXO-1-TRIAZEN-1-YLOXY)PROPANE
(C₂H₅)₂NN₂O₂CH₂CH₂CH₂O₂N₂N(C₂H₅)₂

A partial solution of 1.947 g (0.0126 mol) of 2,2-diethyl-1-nitroso-1-oxyhydrazine sodium salt in 12 ml of anhydrous N,N-dimethylformamide was cooled to 0° C. A solution of 713 μl (0.006 mol) of 1,3-diiodopropane in 12 ml of THF was added dropwise over a period of 30 minutes. The ice bath was removed and the resulting reaction mixture was stirred at 25° C. under argon overnight. To the reaction mixture was added 50 ml of distilled water and then it was extracted with ether. The ether layer was washed with sodium bisulfite solution, dried over sodium sulfate and filtered through a layer of magnesium sulfate. Evaporation of the solvent in vacuo gave 1.16 g of crude product. Purification was carried out by column chromatography on silica-gel; 5:1 methylene chloride:ethyl acetate was used as the eluant. The fractions containing the desired product were combined and evaporated in vacuo to give 966 mg (26%) of 1,3bis(3,3-diethyl-2-oxo-1-triazen-1yloxy)propane: NMR, δ1.086 (t,12H), 2.241 (q,2H), 3.101 (q,8H), 4.385 (t,4H); IR (film), 2980, 2945, 1510, 1459, 1384, 1240, 1065, 1008 cm⁻¹; uv (H20), λ_max (ε), 235 (14,066).

Et₂NN(NO)O⁻Na⁺+I(CH₂)₃I→Et₂NN(O)-NO(CH₂)₃ONN(O)NEt₂

EXAMPLE 14

1,2-BIS(3,3-DIETHYL-2-OXO-1-TRIAZEN-1-YLOXY)ETHANE
$(C_2H_5)_2NN_2O_2CH_2CH_2O_2N_2N(C_2H_5)_2$

Step 1: A partial solution of 2.7 g (17.4 mmol) of 2,2-diethyl-1-nitroso-1oxyhydrazine sodium salt in 17 ml of DMF was cooled to 0° C. under a stream of nitrogen. A solution of 1.4 ml of 1,2-dibromoethane in anhydrous THF was added dropwise. Once addition was complete, the ice bath was removed, and the resulting mixture was stirred at 25° C. overnight. To the reaction mixture was added 200 ml of water and the product was extracted with ether. The organic layer was separated and washed with water. The solution was dried over sodium sulfate and filtered through a layer of magnesium sulfate. Evaporation of the solvent gave 2.1 g of crude product. The product was chromatographed through silica gel and eluted with dichloromethane to give 706 mg of pure 1-(2-bromoethoxy)-2-oxo-3,3-diethyl-1-triazene: IR (film) 2980, 2965, 2880, 1510, 1500, 1450, 1383, 1241, 1235, 1070, 1005 cm$^{-1}$; NMR (CDCl$_3$), δ1.104 (t,6H), 3.124 (q,4H), 3.582 (t,2H), 4.522 (m,2H); uv, $\lambda_{max}(\epsilon)$, 233 (8,977); MS, m/z (%), 242 (MH+, $^{81}$Br, 8), 240 (M+, $^{79}$Br, 9), 224 (4), 223 (4), (37), 209 (36), 132 (41), 109 (56), 107 (56), 101 (64), 102 (100), 84 (32), 72 (32), 56 (36). Exact mass: calculated for C$_6$H$_{14}$$^{81}$BrN$_3$O$_2$, 242.0327, and for C$_6$H$_{14}$$^{79}$BrN$_3$O$_2$, 240.0347; found for MH+, 242.0356 and 240.0417.

Step 2: To a solution of 1.27 g (8.2 mmol) of 2,2-diethyl-1-nitroso-1-oxyhydrazine sodium salt in 5 ml of DMF was added a solution of 425 mg (1.7 mmol) of 1-(2-bromoethoxy)-2-oxo-3,3-diethyl-1-triazene in 5 ml of THF, and the resulting solution was stirred at 25° C. overnight. To the reaction mixture was added 100 ml of distilled water, and the product was extracted in pentane. The organic layer was dried over sodium sulfate and filtered through a layer of magnesium sulfate and the solvent was removed on a rotary evaporator to give 476 mg of crude product. The crude material was purified on dry-packed silica gel Activity III, eluted with 5:1 dichloromethane:ethyl acetate to give pure 1,2-bis(3,3-diethyl-2-oxo-1-triazen-1-yloxy)ethane: NMR, δ1.095 (t,12H), 3.113 (q,8H), 4.50 (s, 4H); uv, H20, $\lambda_{max}$ (ε), 232 (15,083); MS/, m/z (%), 292 (0.4), 132 (15), 103 (30), 102 (100), 87 (7), 86 (2), 85 (5), 75 (5), 74 (2), 72 (11), 71 (4), 70 (2), 58 (7), 57 (17), 56 (20), 47 (2) 45 (7), 44 (87), 43 (6), 42 (25) . Exact mass: calculated for C$_{10}$H$_{24}$N$_6$O$_4$, 292.1854; found for M+, 292.1911.

Step 1

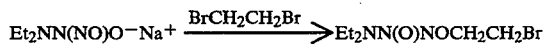

Step 2

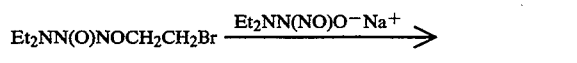

EXAMPLE 15

1-VINYLOXY-2-OXO-3,3-DIETHYL-1-TRIAZENE
$(C_2H_5)_2NN_2O_2CH=CH_2$

A solution of 100 mg of 1-(2-bromoethoxy)-2-oxo-3,3-diethyl-1-triazene (Example 14, step 1) in 5 ml of anhydrous THF was heated at reflux for 24 hours with 200 mg of powdered sodium hydroxide. The solution was filtered and the solvent was evaporated to give 66 mg of product: IR (film), 3080, 2985, 2940, 2880, 1640, 1518, 1500, 1442, 1388, 1245, 1170, 1145, 1016, 950, 860 cm$^{-1}$; NMR, 1.130 (t,6H), 3. 219 (q,4H), 4. 437 (q,1H), 4. 898 (q,1H), 6. 9075 (q,1H).

EXAMPLE 16

1-DIMETHYLAMINOSULFONYLOXY-2-OXO-3,3-DIETHYL-1-TRIAZENE
$[(CH_2H_5)_2NN.O_2SO_2N(CH_3)_2]$

A slurry of 2.54 g (0.0164 mol) of 2,2-diethyl-1nitroso-1-oxyhydrazine sodium salt in 20 ml of anhydrous tetrahydrofuran was cooled to 0° C. To this was added 1.72 ml (0.016 mol) of dimethyl sulfamoyl chloride. The mixture was stirred at room temperature for 24 h and filtered. The filtrate was washed with 10% aqueous sodium hydroxide, dried over sodium sulfate and evaporated under reduced pressure to give 2.1 g of a product mixture. The crude product was purified on silica gel and eluted with dichloromethane: NMR δ1.20 (t,6H), 3.03 (s,6H), 3.52 (q,4H); uv, λmax (ε), 260 nm (7,306) and 217 nm (7,713); IR(film) 2985, 2940, 1460, 1390, 1250, 1185, 1159, 985, 960, 940, 860, 750 cm$^{-1}$. Analysis: C,H,N. Calculated for C$_6$H$_{16}$N$_4$O$_4$S: C, 30.00%; H, 6.66%; N, 23.33%. Found: C, 30.09%; H, 6.72%; N, 23.30% .

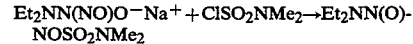

Novel Synthesis Processes

In preparing some of the Formula (I) compounds of the above Examples, there were used novel synthesis processes. The following comments are provided in order to fully disclose these novel synthesis processes. In the first and second novel synthesis processes described below, compounds of Formula (I) wherein R$_1$ and R$_2$ are not identical can be prepared. The above Examples 9A and 10 illustrate the two methods. In the third novel synthesis method disclosed below compounds of Formula (I) wherein R$_3$ is a group of the formula —(CH$_2$)$_n$O(NO)NNR$_1$R$_2$ are prepared. The third process is illustrated in the above Example 14.

First Novel Synthesis Process

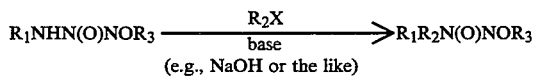

In the above reaction scheme R$_1$, R$_2$ and R$_3$ are as defined in Formula I, and X is the leaving group for the electrophile R$_2$ (e.g., halo). The reaction is allowed to take place in an appropriate solvent (e.g., 3:1 anhydrous THF:DMF, or the like) at about room temperature (about 25° C.).

Second Novel Synthesis Process

A solution of an unsymmetrical secondary amine of the formula R$_1$R$_2$NH in an appropriate solvent (e.g., petroleum ether) is charged with nitric oxide (at about 60 psi and at about −80° C.). The unstable complex that precipitates out of solution is not isolated, but instead is treated with sodium methoxide in methanol (or a like compound in an appropriate solvent). This is followed by reacting with an appropriate electrophile at about 0° C. There is obtained a compound of formula I wherein $R_1$ and $R_2$ are not identical and $R_3$ is an alkyl moiety.

Third Novel Synthesis Process

A process for preparing a compound of Formula (I) wherein $R_3$ is $-(CH_2)_n ONN(O)NR_1R_2$ wherein n is an integer of from 2 to 8 and $R_1$ and $R_2$ are as defined in Formula I. In the process, a compound of the Formula $R_1R_2N(NO)NO^-M^+$ (wherein $M^+$ is an alkali metal ion) is slurried in an appropriate solvent (e.g., THF) and treated at about 0° C. with a bifunctional electrophile of the Formula $X(CH_2)_nX$, wherein X is halo or another leaving group. Thereafter, the temperature is allowed to rise to about room temperature (about 25° C.).

Pharmacological Testing

Effects of Drugs on Mean Arterial Pressure (MAP) and Aortic Diameter

The effects of the compounds of Formula I on the MAP of male Sprague-Dawley rats were measured using a pressure transducer connected to the left carotid artery via a catheter containing heparinized saline. The MAP was recorded on a Grass Recorder. The rat was anesthetized with nembutal at an initial dose of 35 mg/kg and recurrent smaller injections as needed. The test substance was dissolved in 0.9% sodium chloride and injected at the doses shown below into the rat via a catheter in the left jugular vein. The effects on the MAP are recorded in Table I.

TABLE I

Hypotensive Effects of 1-Alkoxy-2-oxo-3,3-dialkyl-1-triazenes[1]

| Drug | Dose (μmol/kg) | MAP (in mmHg) | | |
|---|---|---|---|---|
| | | Initial | Minimum | Final[2] |
| $Et_2N-N\Rightarrow O$ <br> $\parallel$ <br> $N-O(n\text{-}Pr)$ | 40 <br> 35 | 84 <br> 108 | 49 <br> 54 | 56 (at 69 min) <br> 91 (at 47 min) |
| $Et_2N-N\Rightarrow O$ <br> $\parallel$ <br> $N-OMe$ | 45 | 102 | 56 | 84 (at 35 min) |
| $Et_2N-N\Rightarrow O$ <br> $\parallel$ <br> $N-OEt$ | 28 | 108 | 85 | (lasted at least 1 hour) |

[1] The ethoxy derivative was tested in a male Wistar Kyoto rat that had not been anesthetized. The drug was administered by intravenous bolus after dissolution in 5% dextrose. The pressure transducer was connected to the right carotid artery and the MAP was recorded on a Grass Model 2800 8-channel recorder.
[2] Time post-injection is indicated in parentheses.

In the tests of Table I, SNP (i.e., sodium nitroprusside) was used as a control. It is a known, clinically useful vasodilator, but it had a much shorter duration of action than the compounds of Table I. The results show that the compounds of Table I are long-acting antihypertensive agents, decreasing the blood pressure significantly for a prolonged period.

In contrast to the data of Table I, two other rats also received i.v. doses of $Et_2NN(O)NOMe$ and/or $Et_2N-N(O)NOEt$ but the doses of the drugs produced no effect on their MAP. Though these rats gave indications of compromised responsiveness (for example, one animal had experienced a severe ischemic episode earlier in the test day resulting from an accidental penetration of the lungs during a gavage experiment), it was decided to confirm the inherent activity of $Et_2NN(O)$-NOEt as a vasorelaxant by testing it via a standard isolated vascular ring preparation. Thoracic aortic rings from New Zealand White rabbits were suspended in pH 7.4 buffer at 37° C. and a 10-g preload was applied to each. After equilibration for 2 hours, the rings were preconstricted with norepinephrine. By measuring the grams of relaxation induced by adding the $Et_2NN(O)$-NOEt to the organ baths at successively increasing concentrations from $10^{-9}$ to $10^{-3}M$, a dose-response curve was constructed for the compound (see FIG. 1). All three rings studied showed significant vasorelaxation at concentrations of $10^{-7}$ to $10^{-3}M$. We conclude that the compound does indeed exert a reproducible and reliable vasorelaxant effect useful in the treatment of hypertension.

In an in vivo test with rabbits, the acetal derivative synthesized in Example 6 above was also proven active. The compound (11.4 mg) was dissolved in 1.0 ml of phosphate buffered saline and 0.9 ml was injected intravenously into a 6.5 pound New Zealand White rabbit. Hemodynamic data were collected in the rabbit using a procedure similar to that employed in the rat studies of Table I. At this dose of 20 μmol/kg, the blood pressure behaved as indicated in Table II, with MAP falling very rapidly to a low plateau and staying down until the experiment was terminated 15 minutes after injection.

TABLE II

Hypotensive Effects of 1-(Methoxymethyleneoxy)-2-oxo-3,3-diethyl-1-triazene

| Time following injection | Systolic pressure (mm) | Diastolic pressure (mm) | MAP (mm) |
|---|---|---|---|
| 0 (baseline values) | 90 | 50 | 66 |
| 1 min | 70 | 25 | 40 |
| 10 min | 68 | 20 | 32 |
| 15 min | 70 | 25 | 36 |

The compounds of this invention are useful in a method of treating any cardiovascular disorder that will respond favorably to a decrease in blood pressure. These disorders include chronic hypertension, hypertensive crisis, acute congestive heart failure, angina, acute myocardial infarction, left ventricular failure, cerebrovascular insufficiency, and intracranial hemorrhage. It is thought that these long-acting drugs may be advantageously administered orally for treatment of chronic disorders.

Pharmaceutical Compositions

The pharmaceutical compositions of the invention are comprised of an effective amount of a compound of formula I and a pharmaceutical carrier therefor. The carrier can be any of those conventionally used and is limited only by physicochemical considerations such as stability and solubility. For intravenous administration, the carrier will be a sterile aqueous carrier and may contain solubilizing agents, buffers, preservatives, antioxidants, chelating agents, and agents to control the tonicity, such as dextrose or sodium chloride. The requirements for effective pharmaceutical carriers for injectable compositions are well known by one of ordinary skill in this art. (See "Pharmaceutics and Pharmacy Practice", J. B. Lippincott Company, Philadelphia, 1982, edited by Banker and Chalmers, pages 238–250, which are incorporated by reference; also see ASHP "Handbook on Injectable Drugs", 4th edition, by Trissel, pages 622-630, which lists commercially available intravenous infusion solutions; these pages are incorporated by reference.) The compounds may also be formulated as inclusion complexes, such as, for example, cyclodextrin inclusion complexes, or the compounds may be carried within liposomes. Preferred pharmaceutical carriers for injection are phosphate buffered saline, 5% dextrose, and sterile water. Oral administration may also be by standard methods well known to those with ordinary skill in the art, such as capsules, tablets or ingestible liquids utilizing excipients generally used for such purposes (e.g., cornstarch, microcrystalline cellulose, PVP, lactose, stearic acid, purified water U.S.P., and the like).

When the compounds of the present invention are administered to a patient in need thereof, it is thought that a suitable dosage for lowering blood pressure in a patient is from about 0.01 to 100 mg/kg (preferably about 0.1 to 50 mg/kg) of the patient's body weight, regardless of the route of administration or the exact cardiovascular disorder encountered. Administration of such dosages from one to eight times daily (preferably one to four times daily) is contemplated. In order to provide such dosages of the Formula I compounds, it is considered advantageous that solid or liquid unit dosage forms containing about 0.01 to 30 mg (preferably 0.1 to 15 mg) of one of the Formula I compounds be administered to a patient in need thereof from 1 to 8 times daily (preferably from one to four times daily).

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A pharmaceutical composition, comprising: an effective amount of a compound of the formula:

$$R_1R_2N-N\rightarrow O$$
$$\parallel$$
$$N-OR_3$$

wherein:
R$_1$ and R$_2$ are the same or different and are selected from the group consisting of:
C$_{1-12}$ straight chain alkyl,
C$_{1-12}$ straight chain alkyl substituted by alkoxy or acyloxy,
C$_{2-12}$ straight chain alkyl substituted by hydroxy or halo,
C$_{3-12}$ branched chain alkyl,
C$_{3-12}$ branched chain alkyl; substituted by hydroxy, alkoxy, acyloxy or halo,
C$_{3-12}$ straight chain olefinic,
C$_{3-12}$ straight chain olefinic substituted by hydroxy, alkoxy, acyloxy, halo or benzyl,
C$_{3-12}$ branched chain olefinic, and
C$_{3-12}$ branched chain olefinic substituted by hydroxy, alkoxy, acyloxy, halo or benzyl; or
R$_1$ and R$_2$ join together with the nitrogen atom to which they are bonded to form a heterocyclic ring selected from the group consisting of:

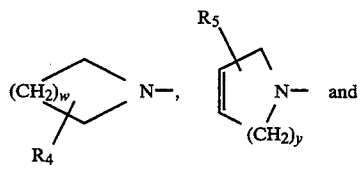

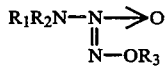

wherein w is 1 to 12, y is 1 or 2, z is 1 to 5, X is NH or O,
R$_4$ is hydrogen, C$_{1-8}$ straight chain alkyl, C$_{3-8}$ branched chain alkyl, C$_{3-8}$ cycloalkyl, or unsubstituted or substituted aryl, and R$_5$ is hydrogen, C$_{1-6}$ straight chain alkyl or C$_{3-6}$ branched chain alkyl; and R$_3$ is selected from the group consisting of
C$_{1-12}$ straight chain alkyl,
C$_{1-12}$ straight chain alkyl substituted by hydroxy, alkoxy, acyloxy or halo,
C$_{3-12}$ branched chain alkyl,
C$_{3-12}$ branched chain alkyl substituted by hydroxy, alkoxy, acyloxy or halo,
C$_{2-12}$ straight chain olefinic,
C$_{2-12}$ straight chain olefinic substituted by hydroxy, alkoxy, acyloxy or halo,
C$_{3-12}$ branched chain olefinic,
C$_{3-12}$ branched chain olefinic substituted by hydroxy, alkoxy, acyloxy or halo,
C$_{1-12}$ acyl, a sulfonyl derivative, a sulfinyl derivative, and a sulfenyl derivative; or
R$_3$ is a group of the formula —(CH$_2$)$_n$—ONN-(O)NR$_1$R$_2$, wherein n is an integer of 2–8, and R$_1$ and R$_2$ are as defined above;

with the proviso that at least one of R$_1$, R$_2$ and R$_3$ is an olefinic group or heteroatom-substituted straight or branched chain alkyl group or olefinic group as recited above; and with the further proviso that R$_1$, R$_2$ and R$_3$ do not contain a halo or a hydroxy substituent α to an oxygen or a nitrogen atom; and a pharmaceutically acceptable carrier therefor.

2. A pharmaceutical composition as recited in claim 1, wherein said composition is an injectable composition, and said pharmaceutically acceptable carrier is sterile.

3. A pharmaceutical composition as recited in claim 1, wherein said composition is in the form of a tablet, capsule or an ingestible liquid.

4. A pharmaceutical composition as recited in claim 1, wherein the composition comprises from about 0.01 to 30 mg of the compound of Formula I.

5. A pharmaceutical composition as recited in claim 1, wherein:
R$_1$ and R$_2$ are the same or different and are selected from the group consisting of:
C$_{1-12}$ straight chain alkyl,
C$_{1-12}$ straight chain alkyl substituted by alkoxy or acyloxy,
C$_{2-12}$ straight chain alkyl substituted by hydroxy or halo,
C$_{3-12}$ branched chain alkyl,
C$_{3-12}$ branched chain alkyl substituted by hydroxy, alkoxy, acyloxy or halo, C<sub>3-12</sub> straight chain olefinic,
C<sub>2-12</sub> straight chain olefinic substituted by hydroxy, alkoxy, acyloxy, halo or benzyl,
C<sub>3-12</sub> branched chain olefinic, and
C<sub>3-12</sub> branched chain olefinic substituted by hydroxy, alkoxy, acyloxy, halo or benzyl; and
R$_3$ is selected from the group consisting of
C$_{1-12}$ straight chain alkyl,
C$_{1-12}$ straight chain alkyl substituted by hydroxy, alkoxy, acyloxy or halo,
C$_{3-12}$ branched chain alkyl,
C$_{3-12}$ branched chain alkyl substituted by hydroxy, alkoxy, acyloxy or halo,
C$_{2-12}$ straight chain olefinic,
C$_{2-12}$ straight chain olefinic substituted by hydroxy, alkoxy, acyloxy or halo,
C$_{3-12}$ branched chain olefinic,
C$_{3-12}$ branched chain olefinic substituted by hydroxy, alkoxy, acyloxy or halo,
C$_{3-12}$ acyl, a sulfonyl derivative, a sulfinyl derivative, and a sulfenyl derivative.

6. A pharmaceutical composition as recited in claim 1, wherein said compound is:
1-(2-hydroxypropoxy)-2-oxo-3,3-diethyl-1-triazene,
1-allyloxy-2-oxo-3,3-diethyl-1-triazene,
1-(2-bromoethoxy)-2-oxo-3,3-diethyl-1-triazene,
1-(methoxymethyleneoxy)-2-oxo-3,3-diethyl-1-triazene,
1-(2-hydroxyethoxy)-2-oxo-3,3-diethyl-1-triazene,
1-methoxy-2-oxo-3-isopropyl-3-allyl-1-triazene,
1-methoxy-2-oxo-3-methyl-3-(2-hydroxypropyl)-1-triazene,
1,3-bis(3,3-diethyl-2-oxo-1-triazen-1-yloxy)propane,
1,2-bis(3,3-diethyl-2-oxo-1-triazen-1-yloxy)ethane,
1-vinyloxy-2-oxo-3,3-diethyl-1-triazene, or
1-dimethylaminosulfonyloxy-2-oxo-3,3-diethyl-1-triazene.

7. A pharmaceutical composition as recited in claim 6, wherein said compound is 1-vinyloxy-2-oxo-3,3-diethyl-1-triazene.

8. A method for treating cardiovascular disorders in a patient in need thereof, wherein said disorders may be treated by lowering the patient's blood pressure, the method comprising:
administering to the patient in need thereof, a blood pressure lowering effective amount of a compound of the formula:

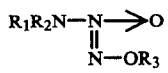

wherein:
R$_1$ and R$_2$ are the same or different and are selected from the group consisting of:
C$_{2-12}$ straight chain alkyl,
C$_{1-12}$ straight chain alkyl substituted by alkoxy or acyloxy,
C$_{2-12}$ straight chain alkyl substituted by hydroxy or halo,
C$_{3-12}$ branched chain alkyl,
C$_{3-12}$ branched chain alkyl substituted hydroxy, alkoxy, acyloxy or halo,
C$_{3-12}$ straight chain olefinic,
C$_{3-12}$ straight chain olefinic substituted by hydroxy, alkoxy, acyloxy, halo or benzyl,
C$_{3-12}$ branched chain olefinic, and
C$_{3-12}$ branched chain olefinic substituted by hydroxy, alkoxy, acyloxy, halo or benzyl; or
R$_1$ and R$_2$ join together with the nitrogen atom to which they are bonded to form a heterocyclic ring selected from the group consisting of:

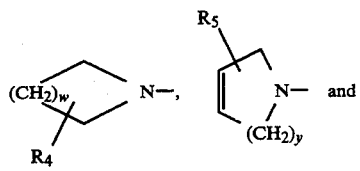

wherein w is 1 to 12, y is 1 or 2, z is 1 to 5, X is NH or O,
R$_4$ is hydrogen, C$_{1-8}$ straight chain alkyl, C$_{3-8}$ branched chain alkyl, C$_{3-8}$ cycloalkyl, or unsubstituted or substituted aryl, and R$_5$ is hydrogen, C straight chain alkyl or C$_{3-6}$ branched chain alkyl; and
R$_3$ is selected from the group consisting of
C$_{1-12}$ straight chain alkyl,
C$_{1-12}$ straight chain alkyl substituted by hydroxy, alkoxy, acyloxy or halo,
C$_{3-12}$ branched chain alkyl,
C$_{3-12}$ branched chain alkyl substituted by hydroxy, alkoxy, acyloxy or halo,
C$_{2-12}$ straight chain olefinic,
C$_{2-12}$ straight chain olefinic substituted by hydroxy, alkoxy, acyloxy or halo,
C$_{3-12}$ branched chain olefinic,
C$_{3-12}$ branched chain olefinic substituted by hydroxy, alkoxy, acyloxy or halo,
C$_{1-12}$ acyl, a sulfonyl derivative, sulfinyl derivative, and a sulfenyl derivative; or
R$_3$ is a group of the formula —(CH$_2$)$_n$ONN(O)NR$_1$R$_2$, wherein n is an integer of 2–8, and R$_1$ and R$_2$ are as defined above;
with the proviso that R$_1$, R$_2$ and R$_3$ do not contain a halo or a hydroxy substituent α to an oxygen or a nitrogen atom; and a pharmaceutically acceptable carrier therefore.

9. The method of claim 8, wherein the cardiovascular disorder treated is chronic hypertension, hypertensive crisis, acute congestive heart failure, angina, acute myocardial infarction, left ventricular failure, cerebrovascular insufficiency or intracranial hemorrhage.

10. The method of claim 8, wherein the cardiovascular disorder is chronic hypertension, hypertensive crisis, acute congestive heart failure or acute myocardial infarction.

11. The method of claim 8, wherein:
R$_1$ and R$_2$ are the same or different and are selected from the group consisting of:
C$_{1-12}$ straight chain alkyl,
C$_{1-12}$ straight chain alkyl substituted by alkoxy or acyloxy,
C$_{1-12}$ straight chain alkyl substituted by hydroxy or halo,
C$_{3-12}$ branched chain alkyl,
C$_{3-12}$ branched chain alkyl substituted by hydroxy, alkoxy, acyloxy or halo, $C_{3-12}$ straight chain olefinic,
$C_{3-12}$ straight chain olefinic substituted by hydroxy, alkoxy, acyloxy, halo or benzyl,
$C_{3-12}$ branched chain olefinic, and
$C_{3-12}$ branched chain olefinic substituted by hydroxy, alkoxy, acyloxy, halo or benzyl; and $R_3$ is selected from the group consisting of
$C_{1-12}$ straight chain alkyl,
$C_{1-12}$ straight chain alkyl substituted by hydroxy, alkoxy, acyloxy or halo,
$C_{3-12}$ branched chain alkyl,
$C_{3-12}$ branched chain alkyl substituted by hydroxy, alkoxy, acyloxy or halo,
$C_{2-12}$ straight chain olefinic,
$C_{2-12}$ straight chain olefinic substituted by hydroxy, alkoxy, acyloxy or halo,
$C_{3-12}$ branched chain olefinic,
$C_{3-12}$ branched chain olefinic substituted by hydroxy, alkoxy, acyloxy or halo,
$C_{1-12}$ acyl, a sulfonyl derivative, sulfinyl derivative, and a sulfenyl derivative.

12. The method of claim 8, wherein said compound is:
1-n-propoxy-2-oxo-3,3-diethyl-1-triazene,
1-methoxy-2-oxo-3,3-diethyl-1-triazene,
1-(2-hydroxypropoxy)-2-oxo-3,3-diethyl-1-triazene,
1-ethoxy-2-oxo-3,3-diethyl-1-triazene,
1-allyloxy-2-oxo-3,3-diethyl-1-triazene,
1-(2-bromoethoxy)-2-oxo-3,3-diethyl-1-triazene,
1-(methoxymethyleneoxy)-2-oxo-3,3-diethyl-1-triazene,
1-(2-hydroxyethoxy)-2-oxo-3,3-diethyl-1-triazene,
1-methoxy-2-oxo-3-isopropyl-3-methyl-1-triazene,
1-methoxy-2-oxo-3-isopropyl-3-allyl-1-triazene,
1-methoxy-2-oxo-3-methyl-3-(2-hydroxypropyl)-1-triazene,
1,3-bis(3,3-diethyl-2-oxo-1-triazen-1-yloxy)propane,
1,2-bis(3,3-diethyl-2-oxo-1-triazen-1-yloxy)ethane,
1-vinyloxy-2-oxo-3,3-diethyl-1-triazene, or
1-dimethylaminosulfonyloxy-2-oxo-3,3-diethyl-1-triazene.

13. A method of treating hypertension in a patient in need thereof, said method comprising: administering to the patient a blood pressure lowering effective amount of a compound of the formula:

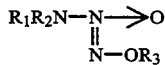

wherein:
$R_1$ and $R_2$ are the same or different and are selected from the group consisting of:
$C_{1-12}$ straight chain alkyl,
$C_{1-12}$ straight chain substituted by alkoxy or acyloxy,
$C_{2-12}$ straight chain alkyl substituted by hydroxy or halo,
$C_{3-12}$ branched chain alkyl,
$C_{3-12}$ branched chain alkyl substituted by hydroxy, or alkoxy, acyloxy or halo,
$C_{3-12}$ straight chain alkyl substituted by hydroxy, alkoxy, acyloxy or halo,
$C_{3-12}$ straight chain olefinic,
$C_{3-12}$ straight chain olefinic substituted by hydroxy, alkoxy, acyloxy, halo or benzyl,
$C_{3-12}$ branched chain olefinic, and $C_{3-12}$ branched chain olefinic substituted by hydroxy, alkoxy, acyloxy, halo or benzyl; or
$R_1$ and $R_2$ join together with the nitrogen atom to which they are bonded to form a heterocyclic ring selected from the group consisting of:

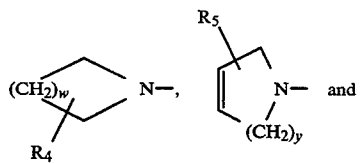

wherein w is 1 to 12, y is 1 or 2, z is 1 to 5, X is NH or O,
$R_4$ is hydrogen, $C_{1-8}$ straight chain alkyl, $C_{3-8}$ branched chain alkyl, $C_{3-8}$ cycloalkyl, or unsubstituted or substituted aryl, and $R_5$ is hydrogen, $C_{1-6}$ straight chain alkyl or $C_{3-6}$ branched chain alkyl; and $R_3$ is selected from the group consisting of
$C_{1-12}$ straight chain alkyl,
$C_{1-12}$ straight chain alkyl substituted by hydroxy, alkoxy, acyloxy or halo,
$C_{3-12}$ branched chain alkyl,
$C_{3-12}$ branched chain alkyl substituted by hydroxy, alkoxy, acyloxy or halo,
$C_{2-12}$ straight chain olefinic,
$C_{2-12}$ straight chain olefinic substituted by hydroxy, alkoxy, acyloxy or halo,
$C_{3-12}$ branched chain olefinic,
$C_{3-12}$ branched chain olefinic substituted by hydroxy, alkoxy, acyloxy or halo,
$C_{1-12}$ acyl, a sulfonyl derivative, sulfinyl derivative, and a sulfenyl derivative; or
$R_3$ is a group of the formula $-(CH_2)_n ONN(O)NR_1R_2$, wherein n is an integer of 2-8, and $R_1$ and $R_2$ are as defined above; with the proviso that $R_1$, $R_2$ and $R_3$ do not contain a halo or a hydroxy substituent $\alpha$ to an oxygen or a nitrogen atom; and a pharmaceutically acceptable carrier therefor.

14. The method of claim 13, wherein:
$R_1$ and $R_2$ are the same or different and are selected from the group consisting of:
$C_{1-12}$ straight chain alkyl,
$C_{1-12}$ straight chain alkyl substituted by alkoxy or acyloxy,
$C_{2-12}$ straight chain alkyl substituted by hydroxy or halo,
$C_{3-12}$ branched chain alkyl,
$C_{3-12}$ branched chain alkyl substituted by hydroxy, alkoxy, acyloxy or halo,
$C_{3-12}$ straight chain olefinic,
$C_{3-12}$ straight chain olefinic substituted by hydroxy, alkoxy, acyloxy, halo or benzyl,
$C_{3-12}$ branched chain olefinic and
$C_{3-12}$ branched chain olefinic substituted by hydroxy, alkoxy, acyloxy, halo or benzyl; and $R_3$ is selected from the group consisting of
$C_{1-12}$ straight chain alkyl,
$C_{1-12}$ straight chain alkyl substituted by hydroxy, alkoxy, acyloxy or halo,

21

C$_{2-12}$ branched chain alkyl,
C$_{3-12}$ branched chain alkyl substituted by hydroxy, alkoxy, acyloxy or halo,
C$_{2-12}$ straight chain olefinic,
C$_{2-12}$ straight chain olefinic substituted by hydroxy, alkoxy, acyloxy or halo,
C$_{3-12}$ branched chain olefinic,
C$_{3-12}$ branched chain olefinic substituted by hydroxy, alkoxy, acyloxy or halo,
C$_{1-12}$ acyl, a sulfonyl derivative, sulfinyl derivative, and a sulfenyl derivative.

15. The method of claim 13, wherein said compound is:
1-n-propoxy-2-oxo-3,3-diethyl-1-triazene,
1-methoxy-2-oxo-3,3-diethyl-1-triazene,
1-(2-hydroxypropoxy)-2-oxo-3,3-diethyl-1-triazene,
1-ethoxy-2-oxo-3,3-diethyl-1-triazene,
1-allyloxy-2-oxo-3,3-diethyl-1-triazene,
1-(2-bromoethoxy)-2-oxo-3,3-diethyl-1-triazene,
1-(methoxymethyleneoxy)-2-oxo-3,3-diethyl-1-triazene,
1-(2-hydroxyethoxy)-2-oxo-3,3-diethyl-1-triazene,
1-methoxy-2-oxo-3-isopropyl-3-methyl-1-triazene,
1-methoxy-2-oxo-3-isopropyl-3-allyl-1-triazene,
1-methoxy-2-oxo-3-methyl-3-(2-hydroxypropyl)-1-triazene,
1,3-bis(3,3-diethyl-2-oxo-1triazen-1yloxy)propane,
1,2-bis(3,3-diethyl-2-oxo-1triazen-1yloxy)ethane,
1-vinyloxy-2-oxo-3,3-diethyl-1-triazene, or
1-dimethylaminosulfonyloxy-2-oxo-3,3-diethyl-1-triazene.

16. A compound having the formula:

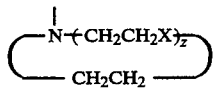

wherein:
R$_1$ and R$_2$ are the same or different and are selected from the group consisting of:
C$_{1-12}$ straight chain alkyl,
C$_{1-12}$ straight chain alkyl substituted by alkoxy or acyloxy,
C$_{2-12}$ straight chain alkyl substituted by hydroxy or halo,
C$_{3-12}$ branched chain alkyl,
C$_{3-12}$ branched chain alkyl substituted by hydroxy, alkoxy, acyloxy or halo,
C$_{3-12}$ straight chain olefinic,
C$_{3-12}$ straight chain olefinic substituted by hydroxy, alkoxy, acyloxy, halo or benzyl,
C$_{3-12}$ branched chain olefinic and
C$_{3-12}$ branched chain olefinic substituted by, hydroxy, alkoxy, acyloxy, halo or benzyl; or
R$_1$ and R$_2$ join together with the nitrogen atom to which they are bonded to form a heterocyclic ring selected from the group consisting of:

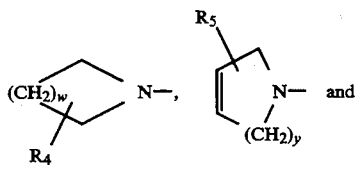

22

-continued

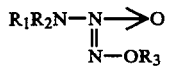

wherein w is 1 to 12, y is 1 or 2, z is 1 to 5, X is NH or O,
R$_4$ is hydrogen, C$_{1-8}$ straight chain alkyl, C$_{3-8}$ branched chain alkyl, C$_{3-8}$ cycloalkyl, or unsubstituted or substituted aryl, and R$_5$ is hydrogen, C$_{1-6}$ straight chain alkyl or C$_{3-6}$ branched chain alkyl; and
R$_3$ is selected from the group consisting of
C$_{1-12}$ straight chain alkyl,
C$_{1-12}$ straight chain alkyl substituted by hydroxy, alkoxy, acyloxy. or halo,
C$_{3-12}$ branched chain alkyl,
C$_{3-12}$ branched chain alkyl substituted by hydroxy, alkoxy, acyloxy or halo,
C$_{2-12}$ straight chain olefinic,
C$_{2-12}$ straight chain olefinic substituted by hydroxy, alkoxy, acyloxy or halo,
C$_{3-12}$ branched chain olefinic,
C$_{3-12}$ branched chain olefinic substituted by hydroxy, alkoxy, acyloxy or halo, a sulfonyl derivative, a sulfinyl derivative, and a sulfenyl derivative; or
R$_3$ is a group of the formula —(CH$_2$)$_n$ONN(O)NR$_1$R$_2$ wherein n is an integer of 2–8, and R$_1$ and R$_2$ are as defined above;
with the proviso that at least one of R$_1$, R2 and R$_3$ is an olefinic group or heteroatom-substituted straight or branched chain alkyl group or olefinic group, as recited above; and with the further proviso that R$_1$, R$_2$ and R$_3$ do not contain a halo or hydroxy substituent $\alpha$ to an oxygen or a nitrogen atom.

17. A compound as recited in claim 16, wherein
R$_1$ and R$_2$ are the same or different and are selected from the group consisting of:
C$_{1-12}$ straight chain alkyl,
C$_{1-12}$ straight chain alkyl substituted by alkoxy or acyloxy,
C$_{2-12}$ straight chain alkyl substituted by hydroxy or halo,
C$_{3-12}$ branched chain alkyl,
C$_{3-12}$ branched chain alkyl substituted by hydroxy, alkoxy, acyloxy or halo,
C$_{3-12}$ straight chain olefinic,
C$_{3-12}$ straight chain olefinic substituted by hydroxy, alkoxy, acyloxy, halo or benzyl,
C$_{3-12}$ branched chain olefinic, and
C$_{3-12}$ branched chain olefinic substituted by hydroxy, alkoxy, acyloxy, halo or benzyl.

18. A compound as recited in claim 16, wherein R$_1$ and R$_2$ are the same or different and are selected from the group consisting of:
C$_{1-12}$ straight chain alkyl substituted by acyloxy,
C$_{2-12}$ straight chain alkyl substituted by hydroxy or halo,
C$_{3-12}$ branched chain alkyl substituted by hydroxy, acyloxy or halo,
C$_{3-12}$ straight chain olefinic,
C$_{3-12}$ straight chain olefinic substituted by hydroxy, acyloxy or halo,
C$_{3-12}$ branched chain olefinic, $C_{3-12}$ branched chain olefinic substituted by hydroxy, acyloxy or halo.

19. A compound as recited in claim 16, wherein $R_1$ and $R_2$ are the same or different and are selected from the group consisting of:
   $C_{1-12}$ straight chain alkyl substituted by acyloxy,
   $C_{2-12}$ straight chain alkyl substituted by hydroxy,
   $C_{3-12}$ branched chain alkyl substituted by hydroxy or acyloxy,
   $C_{3-12}$ straight chain olefinic substituted by hydroxy or acyloxy, and
   $C_{3-12}$ branched chain olefinic substituted by hydroxy or acyloxy.

20. A compound as recited in claim 16, wherein $R_1$ and $R_2$ are the same or different and are selected from the group consisting of:
   $C_{2-12}$ straight chain alkyl substituted by halo,
   $C_{3-12}$ branched chain alkyl substituted by halo,
   $C_{3-12}$ straight chain olefinic substituted by halo, and
   $C_{3-12}$ branched chain olefinic substituted by halo.

21. A compound as recited in claim 16, wherein $R_3$ is selected from the group consisting of
   $C_{1-12}$ straight chain alkyl substituted by hydroxy, alkoxy, acyloxy or halo,
   $C_{3-12}$ branched chain alkyl substituted by hydroxy, alkoxy, acyloxy or halo,
   $C_{2-12}$ straight chain olefinic,
   $C_{2-12}$ straight chain olefinic substituted by hydroxy, alkoxy, acyloxy or halo,
   $C_{3-12}$ branched chain olefinic,
   $C_{3-12}$ branched chain olefinic substituted by hydroxy, alkoxy, acyloxy or halo, and
   a sulfonyl derivative.

22. A compound as recited in claim 16, wherein said compound is:
   1-(2-hydroxypropoxy)-2-oxo-3,3-diethyl-1-triazene,
   1-(2-bromoethoxy)-2-oxo-3,3-diethyl-1-triazene,
   1-(methoxymethyleneoxy)-2-oxo-3,3-diethyl-1-triazene,
   1-(2-hydroxyethoxy)-2-oxo-3,3-diethyl-1-triazene,
   1-methoxy-2-oxo-3-isopropyl-3-allyl-1-triazene,
   1-methoxy-2-oxo-3-methyl-3-(2-hydroxypropyl)-1-triazene,
   1,3-bis(3,3-diethyl-2-oxo-1-triazen-1yloxy)propane,
   1,2-bis(3,3-diethyl-2-oxo-1triazen-1-yloxy)ethane,
   1-vinyloxy-2-oxo-3,3-diethyl-1-triazene, or
   1-dimethylaminosulfonyloxy-2-oxo-3,3-diethyl-1-triazene.

23. A compound as recited in claim 22, wherein said compound is 1-vinyloxy-2-oxo-3,3-diethyl-1-triazene.

24. The method of claim 8, wherein said compound is 1-vinyloxy-2-oxo-3,3-diethyl-1-triazene.

25. The method of claim 13, wherein said compound is 1-vinyloxy-2-oxo-3,3-diethyl-1-triazene.

* * * * *